Aug. 18, 1942. J. D. BROWNELL Plant Pat. 541
ROSE
Filed Dec. 22, 1941
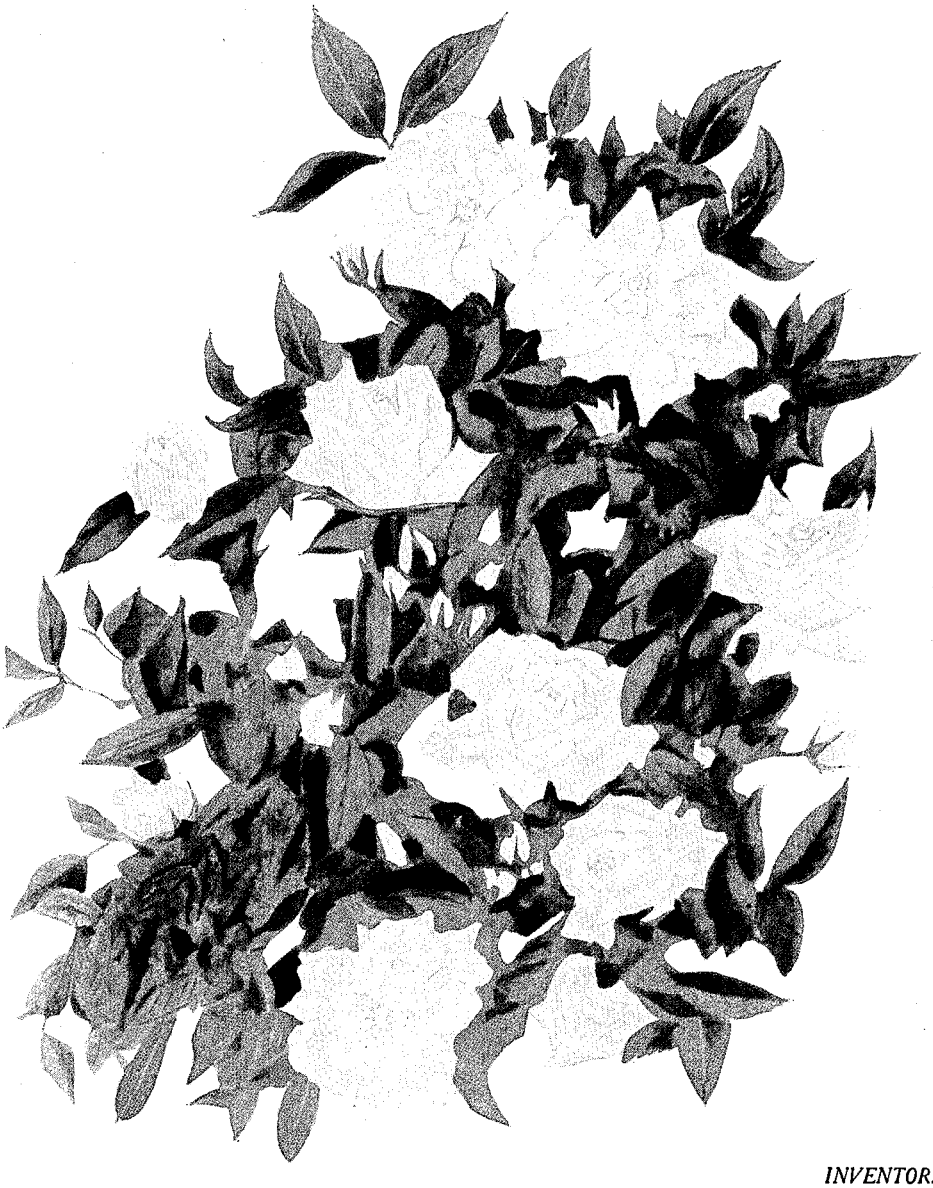
INVENTOR.
Josephine D. Brownell.

Patented Aug. 18, 1942

Plant Pat. 541

UNITED STATES PATENT OFFICE

541

ROSE

Josephine D. Brownell, Little Compton, R. I.

Application December 22, 1941, Serial No. 424,013

1 Claim. (Cl. 47—61)

My invention relates to roses and especially to a new, original and distinct variety, of the class known commercially as hardy climbing roses and to a subdivision of that class which by virtue of a creeping or trailing habit adapts itself also for use as ground cover, wall and fence cover, and embankment decoration, which might be designated as trailing or creeping; also with the habit of growing vigorously held in a nearly upright position over trellis, arbor or other support, produced by me and under my direction in the breeding grounds of my research gardens at Little Compton, Rhode Island, by propagation and by cross pollenation, which can be and has been asexually reproduced.

My new rose is new as to the following characteristics and especially as to their joint association in connection with the characteristics of hardiness or immunity from serious injury on account of cold temperatures prevailing in certain parts of the northern portion of the United States;

The unique yellow nearly self-toned color effect of the petals;

The semi-double character and variation within certain definite limits of the form of the bloom;

Its character of fragrance;

Its climbing or trailing habit in combination with its branching habit.

In the accompanying drawing forming a part of this specification, I have shown my new rose in its natural colors, that is as near as is possible to do so artificially.

I otherwise describe my new rose as follows:

My new rose plant is a hardy hybrid climbing or trailing *Rosa wichuraiana,* crossed in its ancestral generations with, in addition to *Rosa wichuraiana* several so called hybrid tea and specie roses.

My new rose plant is otherwise described as follows.

Essential Information

Type: Hardy climbing to nearly decumbent; outdoor; seedling; for cut flowers, garden decoration, dooryard and roadside display.

Class: Hybrid climbing *wichuraiana;* subdivision climber and creeper or trailer.

*Breeding or discovery*

The pollenation which produced my new rose was directed by me and made July 9, 1936* in my research garden; this seed was planted December 23, 1936, in the greenhouse in Little Compton, Rhode Island, and there germinated in March 1937. The plant therefrom was planted in my said garden in May 1937. This plant can be and has been by me and under my direction asexually reproduced by budding in my said gardens during the months of July and August in the years 1937 to 1941; the characters of the original seedling were thereby reproduced.

The genealogy of my new rose is to the best of my knowledge and belief as follows: pollen of Emily Gray crossed with seed of Yellow Rambler, this resultant seedling was the seed parent and Golden Glow was the pollen parent.

The cross which produced my new rose was made by me under my directions as follows: a flower of the seed parent was emasculated before the opening of any of its anthers, it was promptly covered with a wax paper bag firmly secured at the base as protection against self and foreign pollen. When the stamens were receptive the bag was momentarily removed and the pollen applied with a camel's hair brush and the bag replaced. The hip was picked in November of the same year.

Propagation: It has held its distinguishing characteristics through succeeding clonal generations by budding.

*Flower*

Habit: It blooms outdoors in Little Compton, Rhode Island, in late June and July and begins to bloom about seven days before the climbing rose Dr. W. Van Fleet begins to bloom.

Flowers borne: Usually one to several and when well established frequently fifteen or more on each stem; in regular hybrid tea type of clusters, on strong, stiff, woody stems, notably upright.

Quantity of bloom: Abundant in full sunshine, especially on canes and branches in horizontal or arching position.

Continuity: One season of three to five weeks according to age and size of plant.

Fragrance: Mild, pleasing China tea in combination with *Rosa wichuraiana.*

Bud: Size medium, pointed to slightly ovoid, opens well, being not at all affected by wet or hot weather at Little Compton, Rhode Island.

*Peduncle.*—Medium slightly variable in length, thickness medium, erect and rigid.

*Color**—Calliste Greent with slight variations therefrom variable on different stems. Foliaceous appendages are infrequent.

*This and other dates herein are approximate.

*Color.*—As calyx breaks and bud begins to open outer side of petals are the same color as its pollen parent.

Bloom: Is usually 2½ to 3½ inches when fully open, semidouble with three to four rows of petals, infrequently more or less, and of hybrid tea type of flower, borne in hybrid tea type of cluster recurled except in very dry atmosphere, clearly showing when open most of the pistils and stamens.

*Petals.*—Are in form somewhat variable, outer petals are obovate, inner petals often somewhat narrower, and in many instances one or more petaloids. Texture substantial, both surfaces satiny to shiny.

*Color of opening flower.*—Same as seed parent. The petals usually drop off cleanly.

Reproductive organs:

*Stamens.*—Slightly variable, medium in quantity, slightly variable in length, the anthers are Capucine Yellow.

*Filaments.*—Medium in length and color slightly variable from Capucine Yellow.

*Styles.*—Chalcedony Yellow.

*Ovaries.*—Do not protrude from the calyx lobe when fertilized with its own pollen.

*Plant*

Foliage.—Supremely abundant, due to the fact that the leaves are spaced unusually close together on the stems and branches, and that two or more medium to long and large canes frequently develop from the bloom stems. The leaves are of compound leaflets, frequently of one or three leaflets on stem near the flower and five on lower leaves and usually seven leaflets on the canes and occasionally near base of the larger flower stems.

*Leaves.*—Rounded at the base, slightly narrower than normal and an unusually acute apex. Distinctive characteristics of the leaflets are the form and quantity as above described, their persistence until heavy frost, their shiny surface, and their distinctive green color as hereinafter described; their warped and waving edges, their irregular rather coarse indentation of the serrate edges. The color both sides is similar to the leaflets of the variety "Golden Glow" (Plant Patent 263).

*Rachises.*—Similar to those of the variety "Golden Glow," except they do not usually shade toward any red color.

*Stipules.*—Variable in length frequently notably long averaging on large leaves up to one inch and about one fifth inch wide with thin points which normally spread in relation to each other about 90°, with the thread like tips hooked inward. The edges have minute hairs.

*New canes and branches.*—Medium in size and the color is similar to the under side of the leaves. A distinctive characteristic of the plant growth is that many of the substantial canes grow from bloom stems the same year.

*Prickles on stems, branches and canes.*—Medium in quantity and size and upper edges usually form an angle with the stem cane and branch of about 35°:

The plant requires no dusting, spraying or other control under normal conditions to prevent premature injury or defoliation by blackspot or mildew, the foliage being usually persistent until late fall or heavy frost.

Growth: Habit is repent or creeping, as a trailing vine upon the ground, the canes normally lying in a recumbent to decumbent position, substantially in the manner of its ancestor *Rosa wichuraiana,* due to the trait of the angle of equilibrium of the canes being nearly 90 degrees in relation to the gravitational influence. Canes and branch growth usually starts from side eyes but an eye on the upper surface of a branch or cane can occasionally start to grow usually developing to arch downward and assume the normal growth angle. Neighboring environmental conditions may hold branch growth in abnormal upright position in which the wood will harden. Consequently the habit of growth is not normally quite as prostrate as is that of the species ancestor *Rosa wichuraiana,* but is sufficiently so, that it may be appropriately grown as a ground cover or embankment decoration. About 95% of the cane growth can lie normally recumbent upon the ground and about 5% can lie slightly above, averaging about six inches high; or it can grow tied in the usual positions for growing climbing or pillar roses, blooming freely in all such positions. The new canes in recumbent position may grow fifteen to twenty feet or more in one season, in vertical position they grow much less, laterals therefrom developing vigorously and the vertical growth developing thickness of hard woody growth with abnormal rapidity.

Winter resistance: From tests at Little Compton, Rhode Island, the plant compares in winter resistance with *R. wichuraiana.*

Comparisons: This rose plant is comparable with that of "Golden Glow" except the latter seeks to grow at a higher angle from the horizontal, has a branching habit of fewer strong canes, has less leaves on account also of their wider spacing, has leaflets of a darker color, with surfaces not so warped; all of which in combination are very much inferior and have less desirable and very different resultant effect especially when grown for ground cover, embankment and roadside decoration, over walls and trellises.

The foregoing comparison also applies to a comparison with the variety "Carpet of Gold" number one.

I claim:

The hardy hybrid *Rosa wichuraiana* large flowered climbing and repent rose plant variety with hybrid tea type of flower and bloom cluster, characterized by its resistance to winter injury, its mild pleasing fragrance, with leaflets of a brilliant green, with warped edges, with colors including nearly pure yellow flowers substantially as shown, all especially adapted for ground cover.

JOSEPHINE D. BROWNELL.

*Color reference unless otherwise noted are to Ridgway.